United States Patent
Schindelhauer et al.

(12) 
(10) Patent No.: US 6,331,397 B1
(45) Date of Patent: Dec. 18, 2001

(54) METHOD FOR PRODUCING LONG DNA CONSTRUCTS IN AGAROSE

(76) Inventors: Dirk Schindelhauer, Clemensstr. 111, 80796 München (DE); Howard Cooke, 8 Stirling Road, Edinburgh EH5 3HY (GB)

(*) Notice: Subject to any disclaimer, the term of this patent is extended or adjusted under 35 U.S.C. 154(b) by 0 days.

(21) Appl. No.: 09/423,984

(22) PCT Filed: May 18, 1998

(86) PCT No.: PCT/DE98/01421
§ 371 Date: May 11, 2000
§ 102(e) Date: May 11, 2000

(87) PCT Pub. No.: WO98/53056
PCT Pub. Date: Nov. 26, 1998

(30) Foreign Application Priority Data

May 17, 1997 (DE) .............................................. 197 20 839

(51) Int. Cl.[7] ........................... C12P 19/34; C12N 15/64; C12N 15/10; C07H 21/04; C12Q 1/68

(52) U.S. Cl. ........................ 435/6; 435/320.1; 435/91.4; 435/91.5; 536/23.1

(58) Field of Search ................................ 435/91.4, 320.1, 435/6; 536/23.1

(56) References Cited

PUBLICATIONS

The 1998/1999 BioRad Catalog, pp 219–220, 1999.*
Larin, et al. Methods of Molecular Biology, vol. 54, pp. 1–11, 1995.*

* cited by examiner

*Primary Examiner*—David Guzo
*Assistant Examiner*—Gerald G. Leffers, Jr.
(74) *Attorney, Agent, or Firm*—Steven J. Hultquist

(57) ABSTRACT

The invention relates to a method for producing a DNA construct, whereby two or several DNAs are recombined in melted agarose. The invention also relates to vectors which can be used therefor, in addition to a method for providing large DNAs, especially BACs or PACs.

15 Claims, 18 Drawing Sheets

G438:  5'-GGCCGCGCTAGGGATAACAGGGTAATATA-3'
G439:  5'-GGCCTATATTACCCTGTTATCCCTAGCGC-3'

LPF:   5'-GAAACGGCCTTAACGACGTAGTCG-3'
LPR:   5'-ATGATAAGCTGTCAAACATGAGAATTG-3'

ASal:  5'-GCGAGTCGACAGGGCCTCGTGATACG-3'
ABs:   5'-GATTGCGCGCAGAAAAAAGGATCTC-3'

Kf:    5'-GGAAAACAGCATTCCAGGTATTAG-3'
Kr:    5'-CCATGAGTGACGACTGAATCCG-3'

PT21:  5'-TTAAGGCGCCAAATCTAGAGGATCCGCGCGCAAGAGGTCGACCTAA-3'
PT22:  5'-GTCGACCTCTTGCGCGCGGATCCTCTAGATTTGGCGCC-3'

Fig. 16

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: G438

<400> SEQUENCE: 1
ggccgcgcta gggataacag ggtaatata                                      29

<210> SEQ ID NO 2
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: G439

<400> SEQUENCE: 2
ggcctatatt accctgttat ccctagcgc                                      29

<210> SEQ ID NO 3
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: LPF

<400> SEQUENCE: 3
gaaacggcct taacgacgta gtcg                                           24

<210> SEQ ID NO 4
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: LPR

<400> SEQUENCE: 4
atgataagct gtcaaacatg agaattg                                        27

<210> SEQ ID NO 5
<211> LENGTH: 26
<212> TYPE: DNA
<213> ORGANISM: Artificial Sequence
<220> FEATURE:
```

```
<221> NAME/KEY: misc_feature
<222> LOCATION: ()..()
<223> OTHER INFORMATION: ASa1

<400> SEQUENCE: 5
gcgagtcgac agggcctcgt gatacg                                          26

<210> SEQ ID NO 6
<211> LENGTH: 26
<212> TYPE: DNA
<213> ORGANISM: Artificial Sequence
<220> FEATURE:
<221> NAME/KEY: misc_feature
<222> LOCATION: ()..()
<223> OTHER INFORMATION: Kr

<400> SEQUENCE: 6
gattgcgcgc agaaaaaaag gatctc                                          26

<210> SEQ ID NO 7
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: Kf

<400> SEQUENCE: 7
ggaaaacagc attccaggta ttag                                            24

<210> SEQ ID NO 8
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: Kr

<400> SEQUENCE: 8
ccatgagtga cgactgaatc cg                                              22

<210> SEQ ID NO 9
<211> LENGTH: 46
<212> TYPE: DNA
<213> ORGANISM: Artificial Sequence
<220> FEATURE:
<221> NAME/KEY: misc_feature
<222> LOCATION: ()..()
<223> OTHER INFORMATION: PT21

<400> SEQUENCE: 9
ttaaggcgcc aaatctagag gatccgcgcg caagaggtcg acctaa                    46

<210> SEQ ID NO 10
<211> LENGTH: 38
<212> TYPE: DNA
<213> ORGANISM: Artificial Sequence
<220> FEATURE:
<221> NAME/KEY: misc_feature
<222> LOCATION: ()..()
<223> OTHER INFORMATION: PT22

<400> SEQUENCE: 10
gtcgacctct tgcgcgcgga tcctctagat ttggcgcc                             38
```

METHOD FOR PRODUCING LONG DNA CONSTRUCTS IN AGAROSE

This application is a National Stage application filed under U.S.C. 371 of PCT/DE98/01421, filed May 18, 1998.

The present invention relates to a method for producing long DNA constructs, particularly artificial chromosomes, and vectors usable for this purposes, as well as a method of providing large DNAs, particularly BACs or PACs.

Modern research considers to produce therapeutic proteins in animal cells and transgenic animals, respectively. It is also considered to repair defects of animal, particularly human, cells. In particular, there are considerations of compensating defective genes by corresponding healthy ones. To this end, it is proposed e.g. to integrate the healthy genes in an expressible form into the genome of the cells. It is also taken into account to apply the healthy genes on mammalian (human) artificial chromosomes (hereinafter referred to as MACs (HACs)) and introduce them into the cells. MACs are linear DNAs having a size of several 100 kb. They distinguish themselves by various components. These are per MAC one centromer, two terminal telomeres and a chromosome arm therebetween having at least one origin of replication. The above genes can be applied to the latter component.

However, the production of MACs is accompanied by major problems. Experiments carried out so far to achieve such a production have not been satisfactory In particular, the size of the individual components represents a problem for cloning.

Therefore, it is the object of the present invention to provide a method by which it is possible to produce long DNA constructs, particularly MACs.

According to the invention this is achieved by the subject matters defined in the claims. Thus, the subject matter of the present invention relates to a method and vectors by which long DNA constructs, particularly MACs, can be prepared. A further subject matter of the present invention relates to a method by which large DNAs, e.g. BACs "bacterial artificial chromosomes" or PACs "phage P1 artificial chromosomes", particularly components of MACS, can be provided in great amount and stability.

The present invention is based on the applicant's insights that large DNAs, such as BACs or PACs, can be recombined with one another in melted agarose. He found that MACs can be produced by this if the large DNAs have the individual components of MACs, such as a centromer, e.g. an alpha-satellite DNA, two telomeres, e.g. the sequence $(TTAGGG)_{n=135}$, and a chromosome arm containing at least one 'origin of replication'. He also recognized that bacteria which contain large DNAs, such as BACs or PACs, can be mixed with agarose, so that little agarose blocks are obtained when the agarose has cooled down. The chromosomal DNA of the bacteria can be cleaved therein, while the large DNAs remain uncleaved. To this end, a restriction enzyme is inserted in the little blocks, which cleaves exclusively the bacterial chromosome. It can then be removed from the little blocks by gel electrophoresis, so that only the large DNAs remain in the little blocks. The applicant recognized that the large DNAs as well as the DNA constructs are stable in the little agarose gel blocks and can be stored over a long period of time.

According to the invention, the applicant's insights are used for a method of preparing DNA constructs, comprising the combination of two DNAs by means of recombination in melted agarose.

The expression "DNA construct" refers to a DNA of any kind and length, which can be circular or linear. For example, the DNA is linear and has a length of several 100 kb. The DNA is preferably an artificial mammalian chromosome (MAC).

It is particularly preferred for the MAC to comprise one or several genes whose expression is desired. Examples of such genes are those which in a defective form are connected with diseases, e.g. mucoviscidosis.

The expression "combination by means of recombination" refers to the fact that two DNAs can be recombined with each other. This can be effected by overlapping sequences. It may be favorable for the sequences to comprise recombination-specific sequences such as lox or FRT sequences, the recombination then occurring in the presence of a recombinase, such as Cre or Flp recombinase. The recombination of the two DNAs preferably results in a MAC. In this case, the DNAs comprise all of the elements important for a MAC. Furthermore, they can have one or several genes whose expression is desired. In this connection, reference is made to the above explanations. For example, if a MAC is combined from two DNAs, it can be favorable for one of the DNAs to be present in linear form and the other to be present in circular form. The latter may contain one or several genes whose expression is desired. The linear DNA can contain a centromer and terminal telomeres, which have opposite orientation. The two DNAs can also be present in linear form, each DNA having a telomere which in one DNA is present at the left end and in the other DNA is present at the right end in opposite orientation each. Moreover, the two DNAs can be present in circular form, the circular recombination product having to be linearized by means of recombination cleavage for the development of a MAC.

A further subject matter of the present invention relates to vectors which contain one or several, particularly two, telomeres. Such vectors are suitable to carry out the method according to the invention. Preferred vectors are those which have two telomeres with opposite orientation, e.g. the sequence $(TTAGGG)_{n=135}$, and a recombination-specific sequence located between the telomere beginnings, e.g. lox sequence. Special preference is also given to vectors which also have two resistance genes, one, e.g. kanamycin, being located between the telomere ends, and the other, e.g. ampicillin, being located between the telomere beginnings. Vectors which also have recognition sequences for restriction enzymes which are rare and/or cleave once and several times, respectively, between the telomere beginnings and/or ends are preferred as well. Particularly preferred vectors are the ditelomeric vector PTAT and the monotelomeric vectors PT1, PT1L, PT1LA and PT1LAS. In this connection, reference is made to the examples. The vectors according to the invention can be present as such or in a kit. It can also contain a recombinase, such as Cre or FLP recombinase, and common auxiliary substances, such as buffers, solvents, etc.

A further subject matter of the present invention relates to a method of providing large DNA, particularly BACS or PACs. Such a method comprises the steps of:

(a) mixing a bacterial culture with melted agarose so as to obtain little agarose blocks when the agarose has cooled down, (b) introducing one or several restriction enzymes into the little agarose blocks, the restriction enzymes only cleaving the bacterial chromosome but not the large DNA, and (c) carrying out gel electrophoresis so as to remove the cleaved bacterial chromosome from the little agarose blocks, while the large DNA is retained.

The expression "melted agarose" refers to what is called a 'low melting agarose' which melts at a low temperature.

The expression "gel electrophoresis" refers to the fact that the little agarose blocks are subjected to common gel electrophoresis, particularly pulsed field gel electrophoresis.

In this connection, reference is made to the examples. The expression "large DNA" comprises large extra-chromosomal DNA, e.g. BACs or PACs.

By means of the present invention it is possible to produce long DNA constructs, particularly artificial chromosomes. They can contain desired genes. Furthermore, they can be stored in stable fashion for a long time. Moreover, they can be varied as desired and be rapidly adapted to new requirements. Reference is made explicitly to the examples. Therefore, the present invention represents a breakthrough for the well-calculated treatment of defective genes.

PCYPAC2N-ΔpUC was isolated during the isolation of alpha-satellite clones from the PAC library (Pieter J. deJong, Ioannou, P. A. 1994, Nat. Genet. 6; 84–89) with the alpha-satellite DNA sample X5 (Waye, J. S., et al. 1985 Nucleic Acids Res. 13: 2731–2743) as a vector without insert. The cloning site BamHI and several surrounding restriction sites (NotI, EcoRI, HindIII) were checked and recombinations were ruled out. Furthermore, the clones continue to be sensitive to saccharose-containing medium, which points to an intact sacB gene and its promoter located beyond the cloning site (BamHI, nucleotide position 1 in gene library Acc. No. U09128). The lox site (black triangle) originates from a precursor vector (pAD10SacBII), from which the PAC vector was developed. It has no function in PACs and distinguishes itself from the originally published loxP sequence (sequence positions 2016–2049 of gene library Acc. No. U09128). The lytic replicon of the P1 phage can be reduced using IPTG. The restriction sites NarI (nucleotide position 11991 in U09128), SpeI (position 1605 in U09128), BstXI (position 2917 in U09128) and BrfI (position 3109 in U09128) which were used for further clonings are shown. The 'multicopy' plasmid vector pSXNeo135Isce was equipped with a synthetic IsceI site from complementary oligonucleotides beforehand (oligos G438 and G439). It contains 135 repetitive units of the TTAGGG sequence in tandem series (deLange T., et al. 1990, Mol. Cell. Biol. 10; 518–527) whose function of forming de novo telomeres was confirmed in TACF experiments. The ampicillin resistance gene from vector SP73 (between nucleotide positions 939–2202 of gene library Acc. No. X65333) was amplified by means of primers ASal and ABs. By selection of these primer positions it was guaranteed that the gene contains transcription termination signals at its 3' end but the replication origin based on pBR with many copies per cell (ori) is ruled out. The telomere sequence can be removed by cleavage together with the NotI and IsceI sites located at the telomere sequence end by using ClaI and XbaI and cloned into suitable cleaving sites with given orientation.

Figure 6:
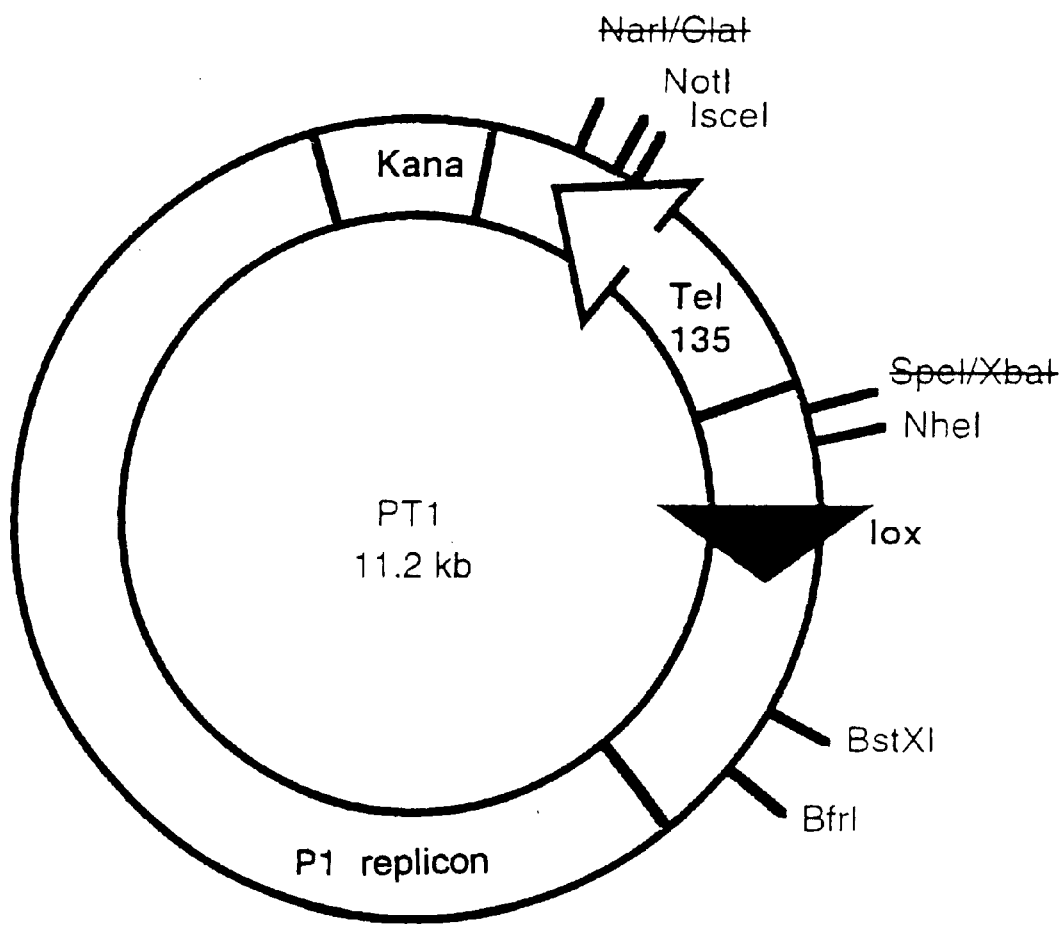

FIG. 6: Map of the monotelomeric vector PT1. By removing by cleavage the lytic replicon and the cloning site of the PAC vector PCYPAC2N-ΔpUC by using the restriction nucleases NarI and SpeI, a 10.3 kb fragment forms which only contains the 'unit copy' P1 phage replicon, the kanamycin resistance gene and the lox site of the PAC vector. It has suitable ends for the cloning of the 0.9 kb telomere sequence removed by cleavage using XbaI/ClaI. All of the restriction recognition sequences are lost at both ends by ligation, so that recloning of the same telomere sequence from the identical gel elution preparation becomes possible at another site. This vector is adapted to clone long genomic fragments into the singular restriction site NheI (between Tel 135 and lox, not shown, at nucleotide position 1716 in gene library Acc. No. U09128) and use them for the combination with a second component carrying a telomere sequence.

Figure 7:
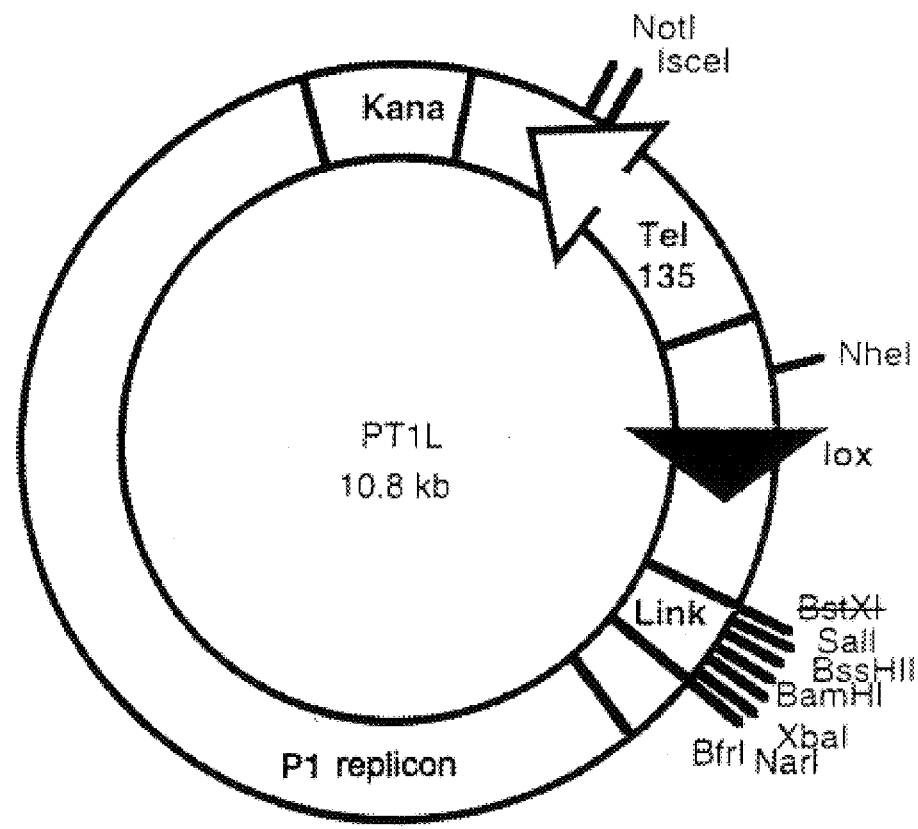

FIG. 7: Map of the monotelomeric vector PT1L. The site directed cloning of the linker synthesized in respect thereto became possible by cleavage of the plasmid PT1 with BfrI (nucleotide position 3309 in gene library Acc. No. U09128) and BstXI (nucleotide position 2917 in gene library Acc. No. U09128). The complementary oligonucleotides PT21 and PT22 serve for producing the linker with suitable restriction sites for cloning the Amp gene and the second identical telomere sequence in opposite direction. By the cloning of the linker the BfrI site was maintained, as intended, whereas the BstXI site disappeared. This vector is adapted to clone long genomic fragments into the singular restriction site NheI (between Tel 135 and lox, not shown, at nucleotide position 1716 in gene library Acc. No. U09128) and use them for the combination with a second component carrying a telomere sequence.

Figure 8:
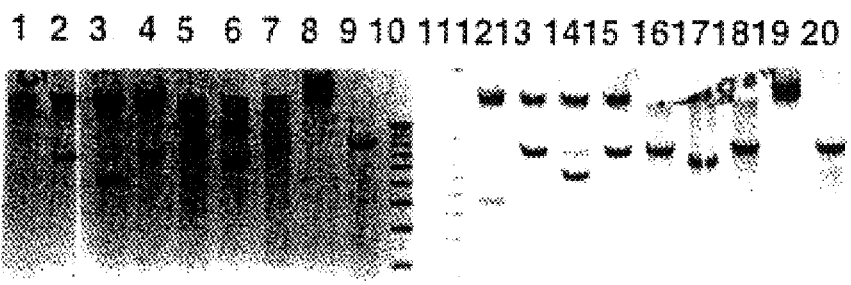

FIG. 8: Checking the newly integrated restriction sites of two clones from the PT1L cloning. Clone No. 8: lanes 1–9, clone No. 12: lanes 12–20, lanes 1, 12: uncleaved plasmid DNA. Lanes 2, 13: NotI; lanes 3, 14: NotI and XbaI, lanes 4, 15: XbaI; lanes 5, 16: SalI; lanes 6, 17: BamHI, lanes 7, 18: BfrI; lanes 8, 19: NarI; lanes 9, 20: BssHII. Lanes 10, 11: 1 kb ladder longitudinal standard from Gibco BRL, the uppermost band corresponds to 12 kb. The cleavage of the NarI site only became possible by the addition of pBR328 DNA as, an activator for the nuclease (cf. FIG. 11).

Figure 9:
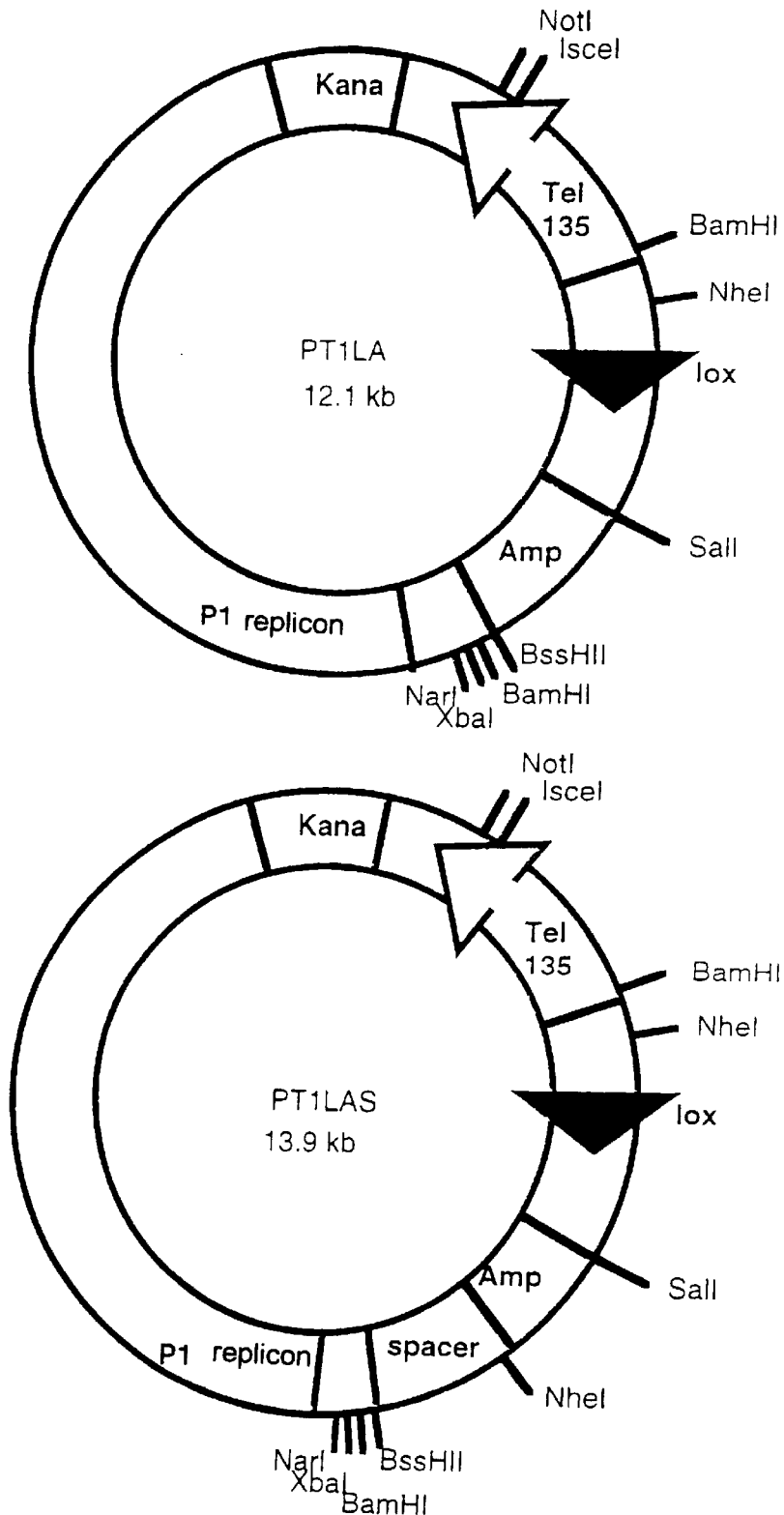

FIG. 9: Map of the monotelomeric vectors PT1LA and PT1LAS. By means of primers ABs and ASal, a 1260 bp fragment which contains the ampicillin resistance gene (corresponds to positions 939–2202 gene library Acc. No. X65333) was amplified from the vector pSXneo135IsceI and cleaved by the restriction nucleases BssHII and SalI whose sites were created with modified primer sequences. The cleaved gel-eluted PCR fragment was ligated with the gel-eluted plasmid PT1L cleaved by BssHII and SalI and cloned. The planned product PT1LA and another product PT1LAS formed, which has integrated an additional sequence of 1.8 kb (spacer). By the additional sequence (spacer) another NheI site was introduced. PT1LA is adapted to clone long genomic fragments into the singular restriction site NheI (between Tel 135 and lox, nucleotide position 1776 in gene library Acc. No. U09128) and use them for the combination with a second component carrying a telomere sequence.

Figure 10:
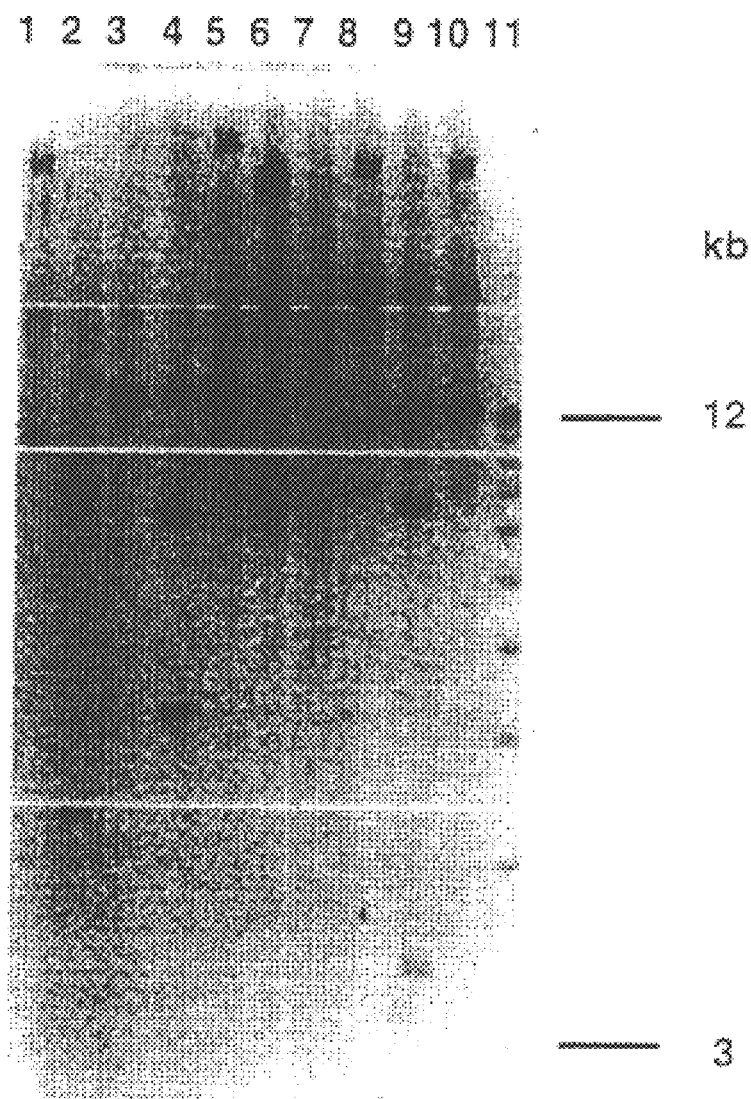

FIG. 10: Checking the vectors PT1LA and PT1LAS by restriction analysis. Agarose gel electrophoresis (0.8%) and ethidium bromide staining. Lanes 1–5: PT1LA; lanes 6–10: PT1LAS; lanes 1, 6: uncleaved plasmid DNA; lanes, 2 7: BamHI; lanes 3, 8: NotI; lanes 4, 9: NotI and XbaI; lanes 5, 10: XbaI, lane 11: 1 kb ladder, Gibco BRL. The small BamHI fragment and the small NotI/XbaI fragment as well as the entire length are longer by 1.8 kb in PT1LAS as compared to TP1LA. The difference between the small BamHI fragments and the small NotI/XbaI fragments of both vectors corresponds to the full length of the 0.9 kb telomere fragment.

Figure 11:
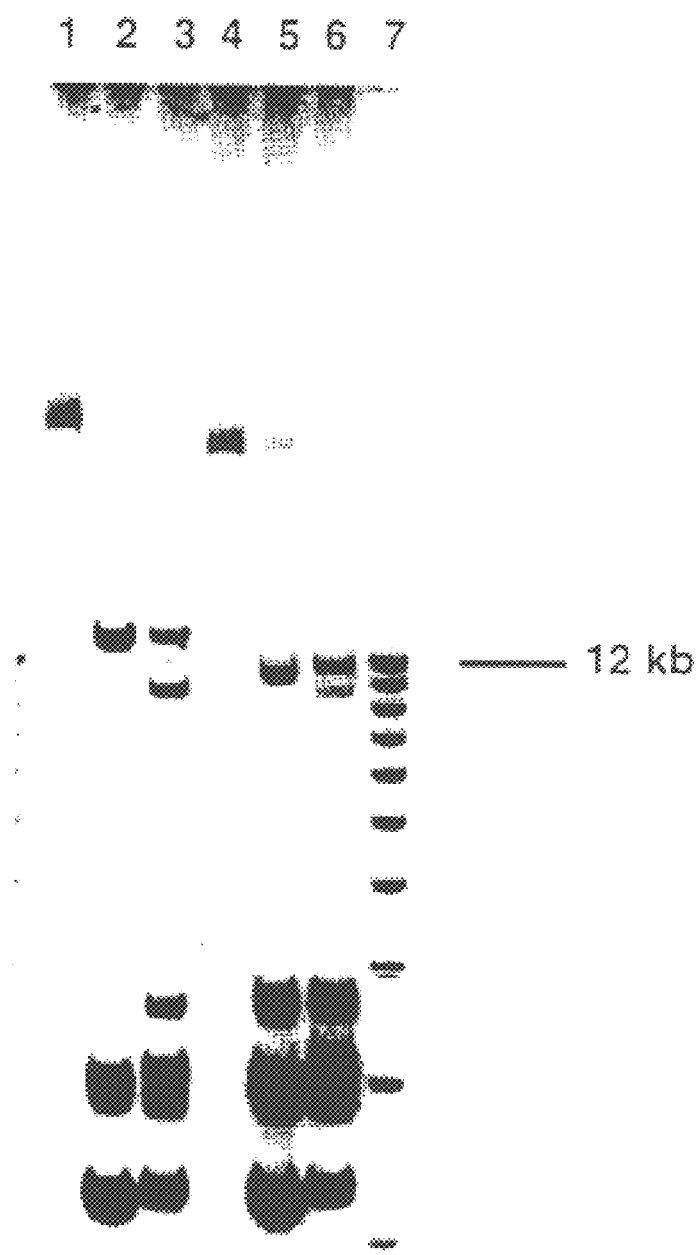

FIG. 11: Activation of the NarI cleavage in the presence of great amounts of pBR328. The NarI site introduced with the synthetic linker cannot be cleaved by NarI as long as no supporting NarI site is offered in cis or trans. Lanes 1–3: PT1LAS; 1: cleaved with NarI alone (uncleaved); 2: cleaved with NarI after ten times the excess of pBR328 plasmid was admixed; 3: cleaved with NarI+pBR328 and SalI; lanes 4–6: PT1LA; 4: cleaved with NarI alone (uncleaved); 5: cleaved with NarI after ten times the excess of pBR328 plasmid was admixed; 6: cleaved with NarI+pBR328 and SalI; lane 7: longitudinal standard 1 kb ladder (Gibco BRL). The localization and the availability of the introduced NarI site was thus checked.

Figure 12:
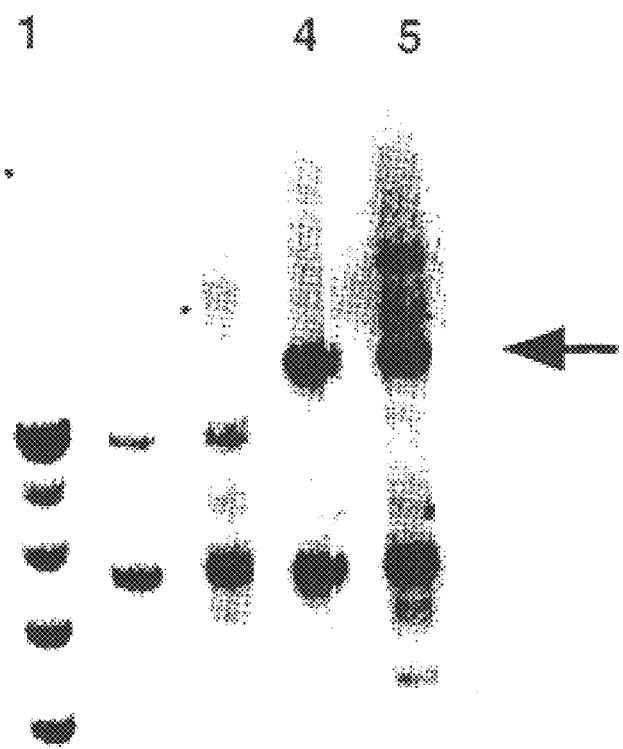

FIG. 12: Checking of the T4 DNA ligation of the second telomere fragment with PT1LAS. 50% of the ligation batch were separated at 30 V in 0.8% agarose for 24 h and stained using ethidium bromide. Lane 4: The reaction mixture without ligase. Lane 5: with ligase. The 13.9 kb NarI/XbaI fragment has taken up monomers (arrow) and oligomers of the 0.9 kb ClaI/XbaI telomere fragment. Lane 1: 1 kb ladder, Gibco BRL, the uppermost band corresponds to a length of 12 kb.

Figure 13:
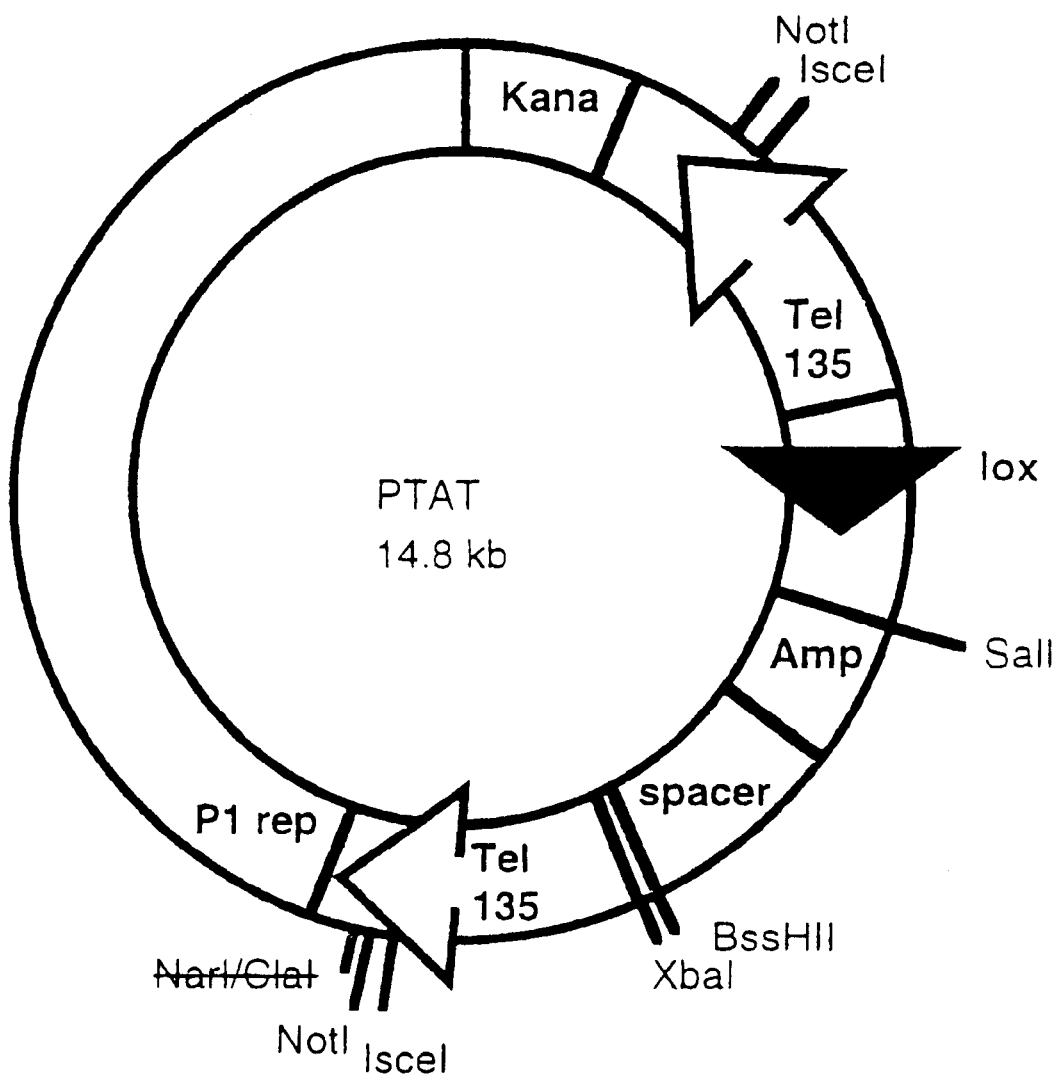

FIG. 13: Map of the ditelomeric vector PTAT. For introducing the second telomere sequence which originates from the identical preparation of the material already used for the cloning of the first telomere sequence and thus contained XbaI and ClaI ends for the site-directed integration, the vector PT1LAS was cleaved with the restriction nucleases NarI and XbaI at the newly integrated recognition sites. The cleavage of the NarI site of the introduced linker had to be activated by the addition of ten times the amount of pBR328 DNA. The NarI and ClaI sites are lost by ligation, whereas the XbaI site is maintained. The restriction cleavage sites NotI (8 bp, rare recognition sequence) and IsceI (17 bp consensus sequence which does virtually not occur, does probably not cleave a single time in the human genome), which are located on the 0.9 kb fragment directly at the telomere sequence ends, are in both cases in planned orientation.

Figure 14:
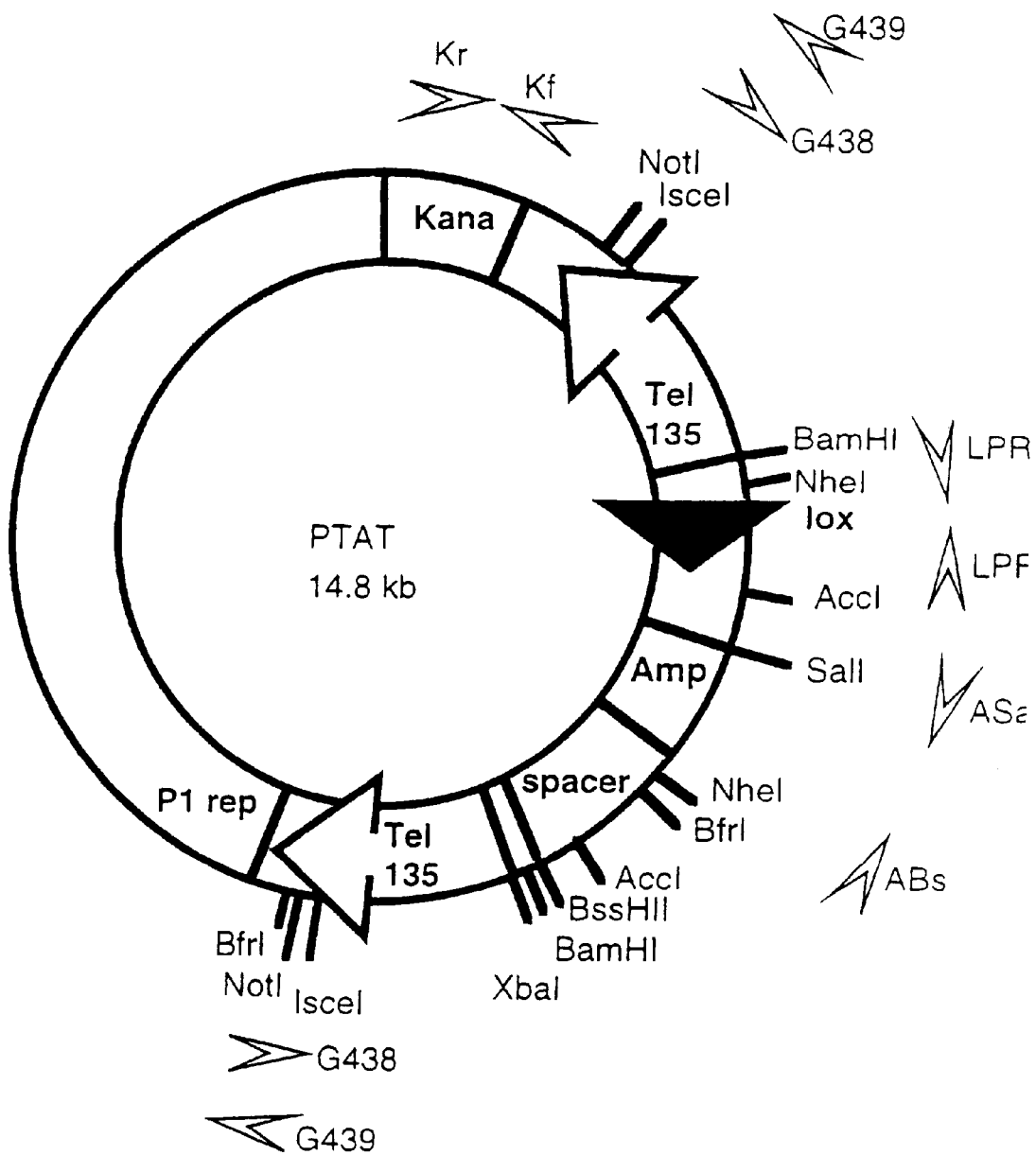

FIG. 14: Restriction map of the ditelomeric vector prototype PTAT. The illustrated restriction sites serve for checking the clonings. The two NotI sites (8 bp rare cutter) as well as the IsceI site (the 17 bp recognition sequence is found extremely seldom, the human genome contains probably no single IsceI site) were integrated together with the telomere sequences (TTAGGG) n=135 on a 0.9 kilobase long fragment. The arrowheads of the telomere sequences (Tel 135) show the direction from 5' to 3' of the G-rich strand. The presence of the BamHI sites at the beginnings of the telomere sequences and the XbaI site at the beginning of the lower telomere sequence, which also originate from the employed 0.9 kb telomere fragment as well as the resulting lengths of 0.9 kb serve as an evidence for the fact that the telomere sequences were integrated completely without deletion. The spacer sequence of 1.8 kb (spacer) has occurred spontaneously in a clone during the cloning of the ampicillin resistance gene. In the order in which they occur in the spacer, the restriction sites of the restriction nucleases AccI, BfrI, NheI cannot be found in one of the employed starting clones (PCYPAC2N-ΔpUC, pSXNeo135IsceI). The origin of the spacer DNA is not known. It could come from the employed *E. coli* strain. By means of the vector PT1LA which only contains the ampicillin resistance gene but no spacer, the cloning of the second telomere sequence failed. The restriction-mapped spacer sequence could have a stabilizing effect on a ditelomeric plasmid. For the further checking of the structure, PCRs were carried out. The following primer pairs yielded the expected products: Kr and Kf; Kr and G439; G438 and LPF; LPF and PLR; LPR and ABs; ASal and ABs; the long PCR ASal and G438 yielded no product (1 min. 95° C., 1 min. 62° C., 4 min. 72° C., 25 cycles, Taq polymerase with manufacturer's buffer from Amersham).

Figure 15:
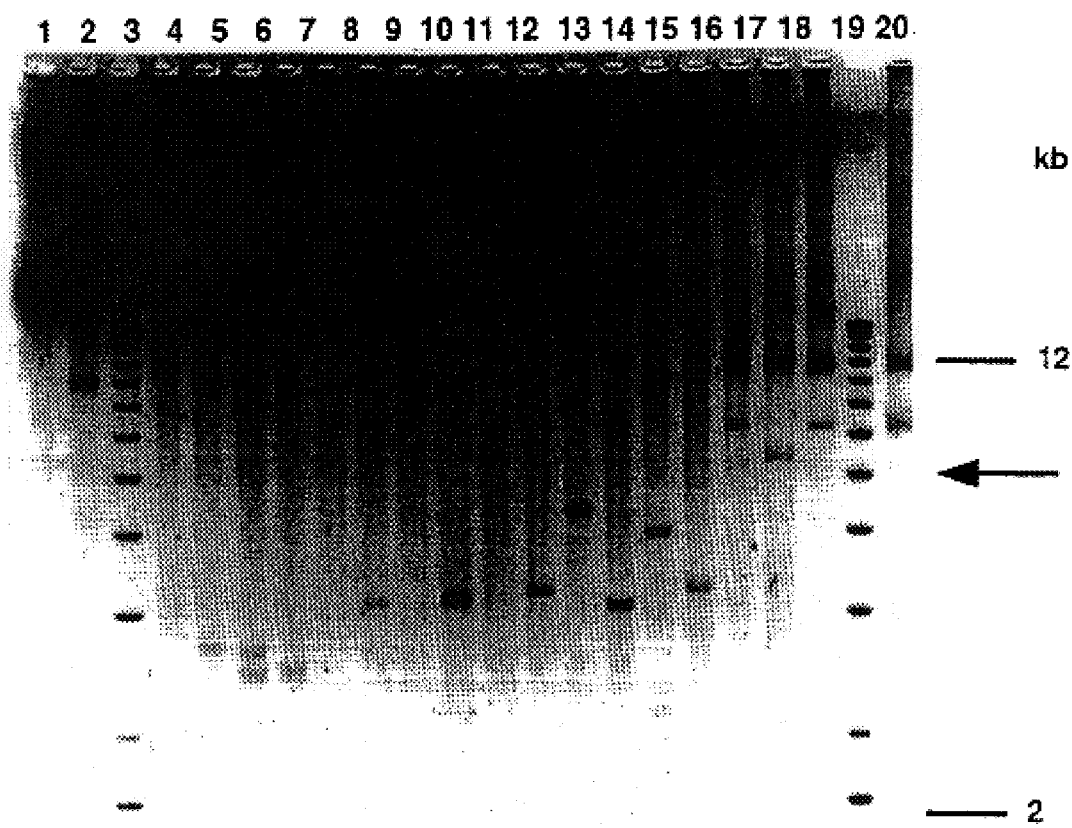

FIG. 15: Checking of the integrity of the ditelomeric vector PTAT by means of restriction analysis: agarose gel electrophoresis 0.8% and ethidium bromide staining. Lanes 1, 19: 1 kb ladder (Gibco BRL.); lane 2: uncleaved plasmid DNA; lanes 3–18: cleaved plasmid DNA with enzymes: 3: BfrI; 4: BfrI and NheI; 5: NheI; 6: XbaI; 7: XbaI and SalI; 8: SalI; 9: SalI and BssHII; 10: BssHII; 11: AccI; 12: BamHI; 13: BamHI and SalI; 14: NotI and SalI; 15: NotI and AceI; 16: NotI and NheI; 17: NotI and BssHII; 18: NotI. In many cleavages, not properly limited bands having running lengths around 8–9 kb can be seen. These bands and the predicted fragments with telomeric sequences hybridize with the 0.9 kb telomere fragment as a sample. The spacer DNA shows unspecific signals with the telomere fragment sample (result not shown). All cleavages correspond to the planned structure of the vector PTAT. The removability by cleavage of the ditelomeric fragment of 6.1 kilobases (arrow) with the nuclease IsceI, which is directly located at the ends of the telomere sequences and occurs extremely seldom with its 17 bp recognition sequence was proved in lane 20.

FIG. 16: The nucleotide sequences of the synthetic primers which served for cloning and checking the cloning of PTAT and its precursors (SEQ ID NOS:1–10).

Figure 17:
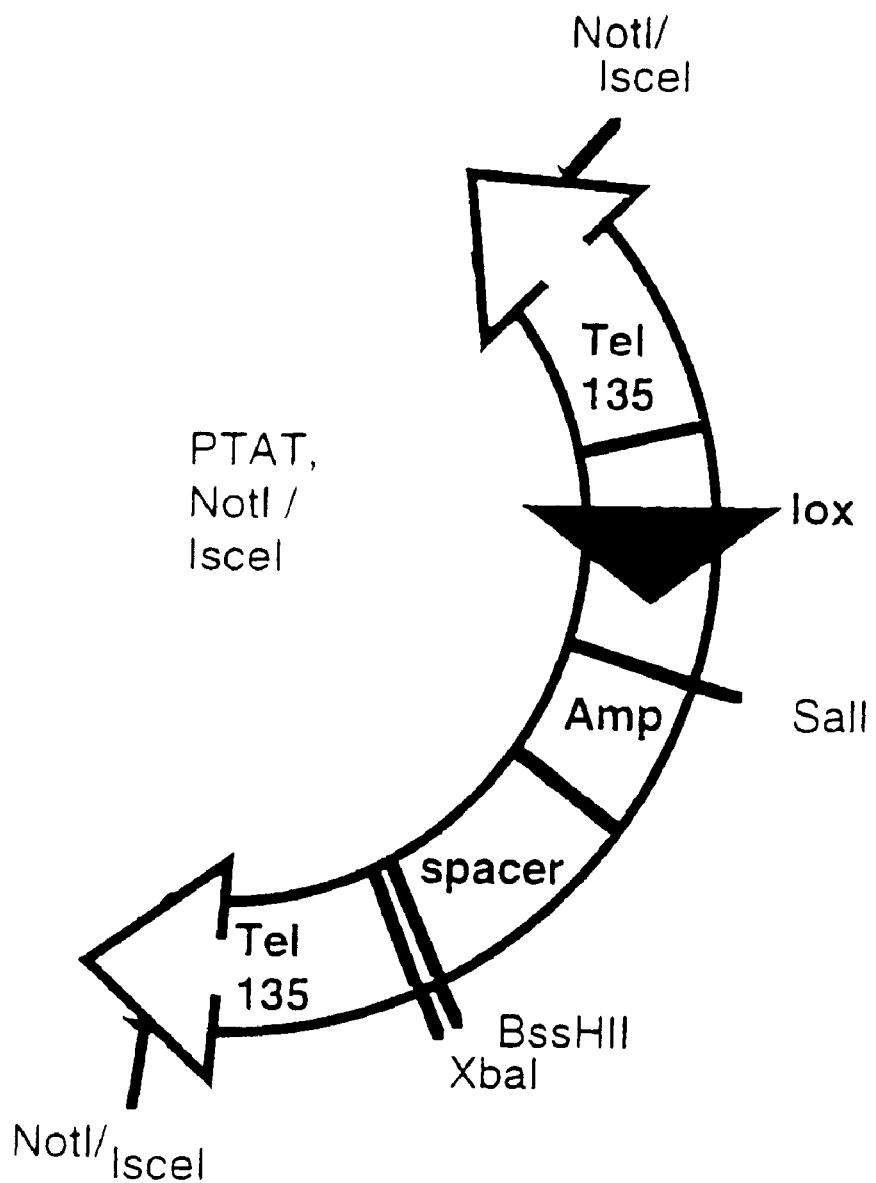

FIG. 17: A 6.1 kilobase long ditelomeric fragment, each having terminal telomere sequences pointing outwards (TTAGGG)n=135 is obtained by cleavage of the vector PTAT with the extremely seldom cleaving restriction nuclease IsceI or the extremely seldom cleaving restriction nuclease NotI. It is known from TACF experiments that de novo telomeres also form if further DNA segments are located outside the telomere sequence end.

Correspondingly, other restriction sites which cleave only once between the telomere sequence ends e.g. in PTAT are also in consideration as nucleases for the release of the telomere sequences. There are various possibilities of cloning additional DNA segments between the telomeres. A small selection of suitable restriction sites which cleave only once in the vector PTAT is shown (SalI, BssHII, XbaI). Moreover, further restriction sites are present which can be used for the partial or full exchange of the intertelomeric section.

Figure 18:
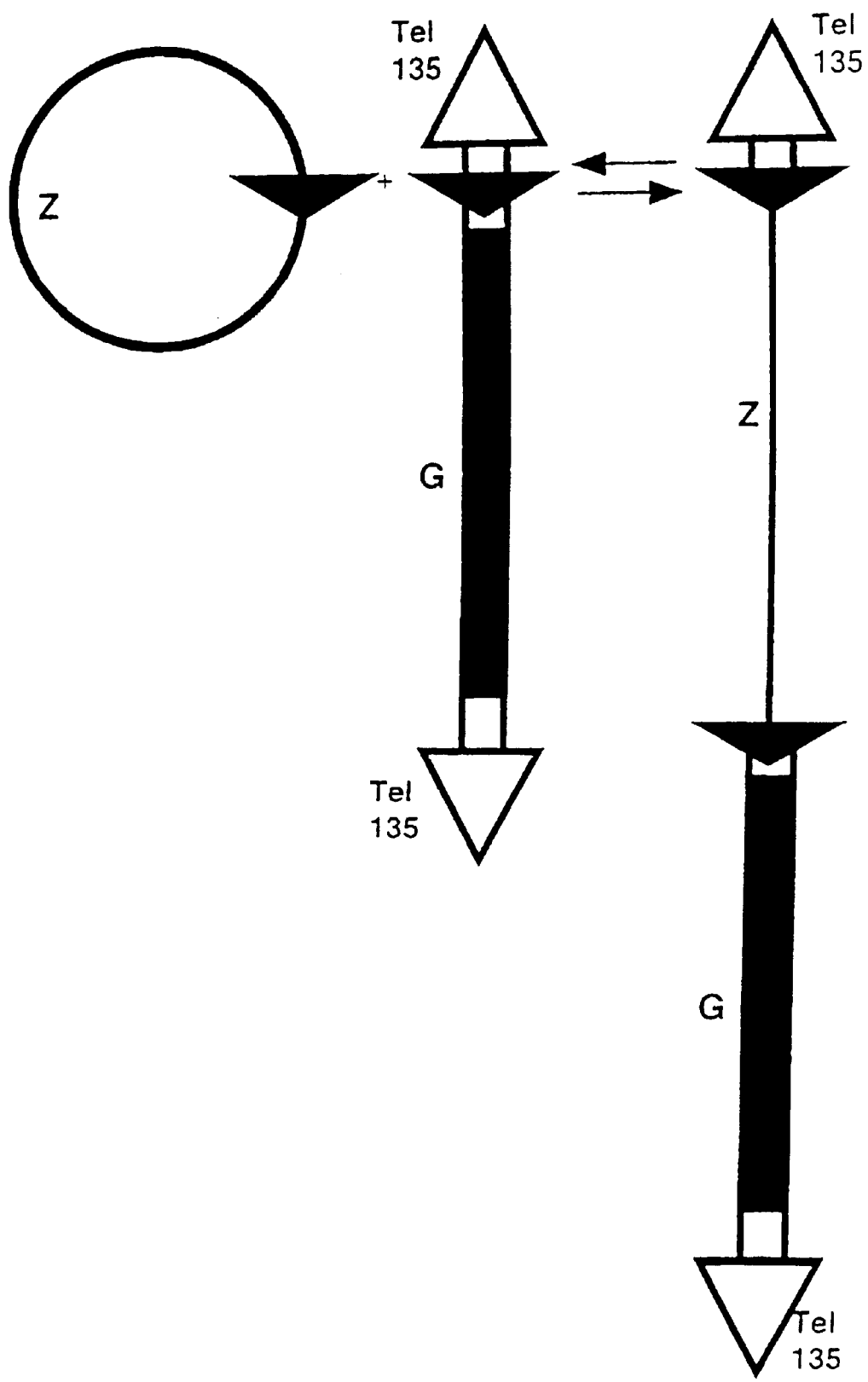

FIG. 18: The cloning of a chromosomal component which consists of a chromosome arm having a gene (G), into the ditelomeric vector PTAT or its descendants, enables the free choice of the centromer component (Z) and its insertion in a single in vitro step. The recombination product consists of joined identical material which need not be analyzed again.

Figure 19:
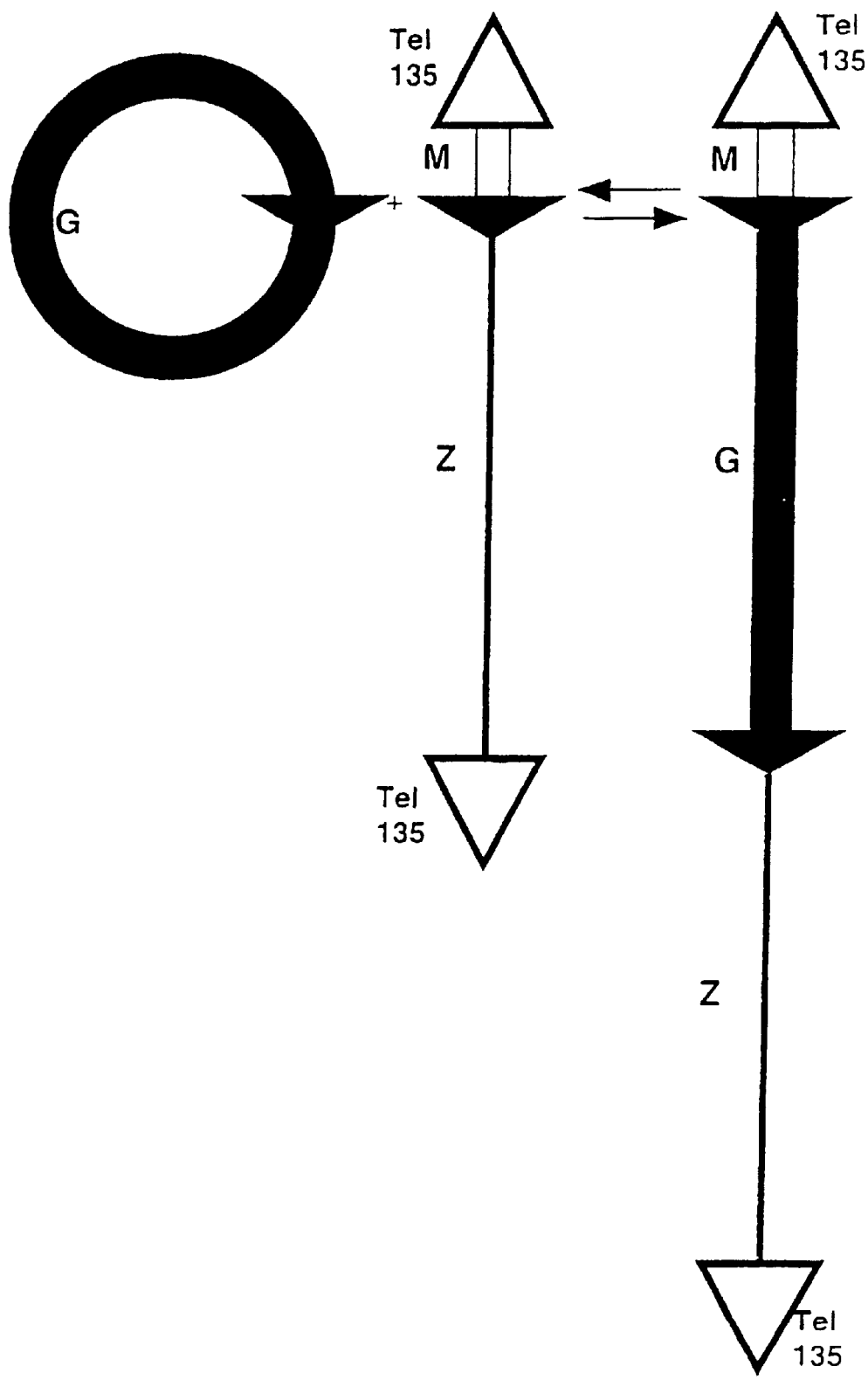

FIG. 19: The cloning of the centromer component (Z) into the ditelomeric vector equipped with one or several markers (M) results in the basic MAC construct TZT. It enables the combination of any circular component (G). Thus, various therapeutic genes can be inserted by means of IGSSR in a single in vitro step in the basic MAC construct. From the insight into the structure of the two substrates the accurate structure of the produced MAC construct follows, without further analyses becoming necessary.

The invention is explained by the following examples:

EXAMPLE 1

Combination of PACs by Means of Lox-Cre Recombinase in Melted Agarose

Recombination is carried out in which a 120 kb long alpha-satellite DNA PAC clone from chromosome X and a 140 kb long alpha satellite DNA PAC clone from chromosome 17 are used jointly with a 95 kb long HPRT (hypoxanthine phosphoribosyltransferase) gene fragment.

(A) Provision of PAC DNA by Means of Little Agarose Blocks

Figure 1:
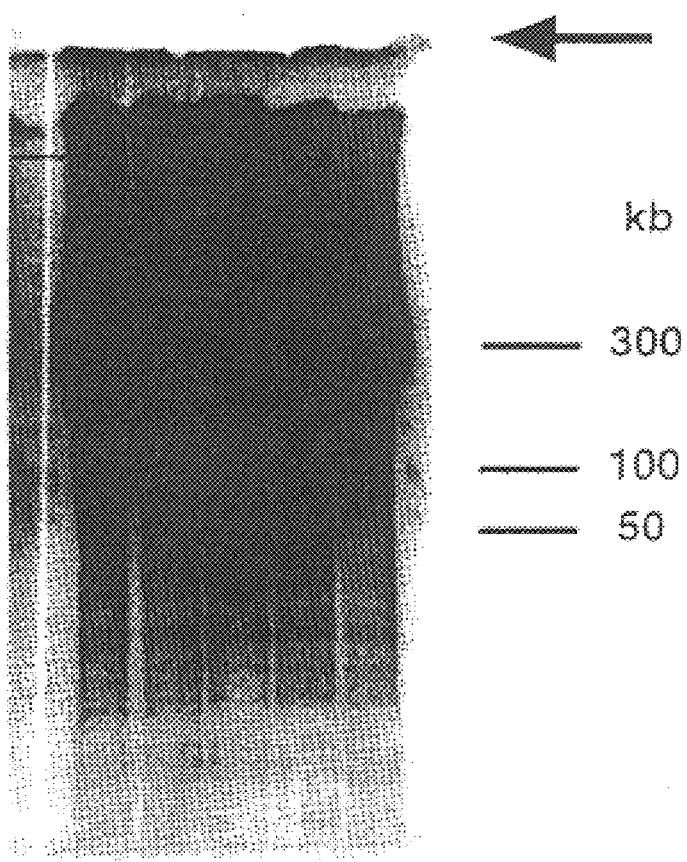
FIG. 1: Provision of concentrated, intact PAC DNA in little agarose gel blocks. Pulsed field gel electrophoresis in 1% agarose and subsequent ethidium bromide staining for checking the cleavage of the *E. coli* chromosomes with the seldom cleaving restriction nuclease AscI. The uncleaved, circular, intact PAC DNA, which does not migrate during the pulsed field gel electrophoresis (16 h, 200 V, 5 to 20 s switching time, 12° C., 0.5×TAE buffer), remains in the little blocks (5 little blocks of the alpha-satellite PAC of chromosome X having a length of 125 kb), which are removed from the gel pocket (arrow) prior to staining and stored in TE. In this way, the high concentration of the PAC DNA in the little blocks remains unchanged during the separation of the *E. coli* DNA. ⅓ of the volume of the little blocks corresponds to the part of bacteria which depending on the number of copies (with or without induction of the lytic replicon of the PACs by IPTG) carry about 2.5 to 10 PAC molecules per cell. The *E. coli* chromosome is about 24 times greater than a PAC clone having 200 kilobases. If the PACs are used as 'unit copy' plasmids (copy number the same as that of the *E. coli* chromosome) without induction of the lytic replicon with IPTG, up to about ¹⁄₂₄ of the amount to be seen (the fragmented *E. coli* chromosome can be seen) can be expected as intact PAC DNA in the little block. These are very large amounts of intact DNA which enable another in vitro manipulation of these long molecules.

The PAC clones are propagated in a final culture volume of 100 ml LB broth (kanamycin selection, IPTG induction). Little bacteria blocks in agarose are produced (Smith, C. L. et al. 1988. In: Davies, K. E. Genome Analysis, IRL Press, Oxford, 41–49). In order to obtain especially high DNA concentrations, 1 volume of bacterial precipitate is mixed with 2 volumes of a 2% LMP agarose (low melting point agarose, Gibco BRL). All of the buffers and solutions are prepared from distilled water containing 0.1 mM EGTA. In order to fragment the E. coli chromosome while the PAC remains intact, the DNA located in the little blocks is treated with a restriction nuclease which no longer cleaves in PAC but cleaves in the E. coli chromosome (in this case AscI ). The restriction cleavage is carried out in the manufacturer's buffer to which 0.75 mM spermidine/3HCl and 0.3 mM spermine/4HCl are added. Thereafter, proteinase-K treatment of the little blocks follows. The little blocks are placed on a 1% agarose gel for pulsed field gel electrophoresis which is not sealed with melted agarose. After a running period of 16 hours at 200 V with increasing switching time from 5–20 s in 0.5×TAE buffer at 12° C., the little blocks which contain circular PAC DNA are freed from the gel pockets again and stored in TE at 4° C. For evaluating the complete cleavage of the E. coli chromosomes, the gel is stained with ethidium bromide. The E. coli fragments show a pattern which is at a marked distance from the gel pockets (FIG. 1). The little blocks contain large plasmids having a concentration which corresponds up to ⅓ of the concentration of the respective plasmid DNA in E. coli (about 1–5 PAC molecules / 1 bacteria volume).

Figure 2:
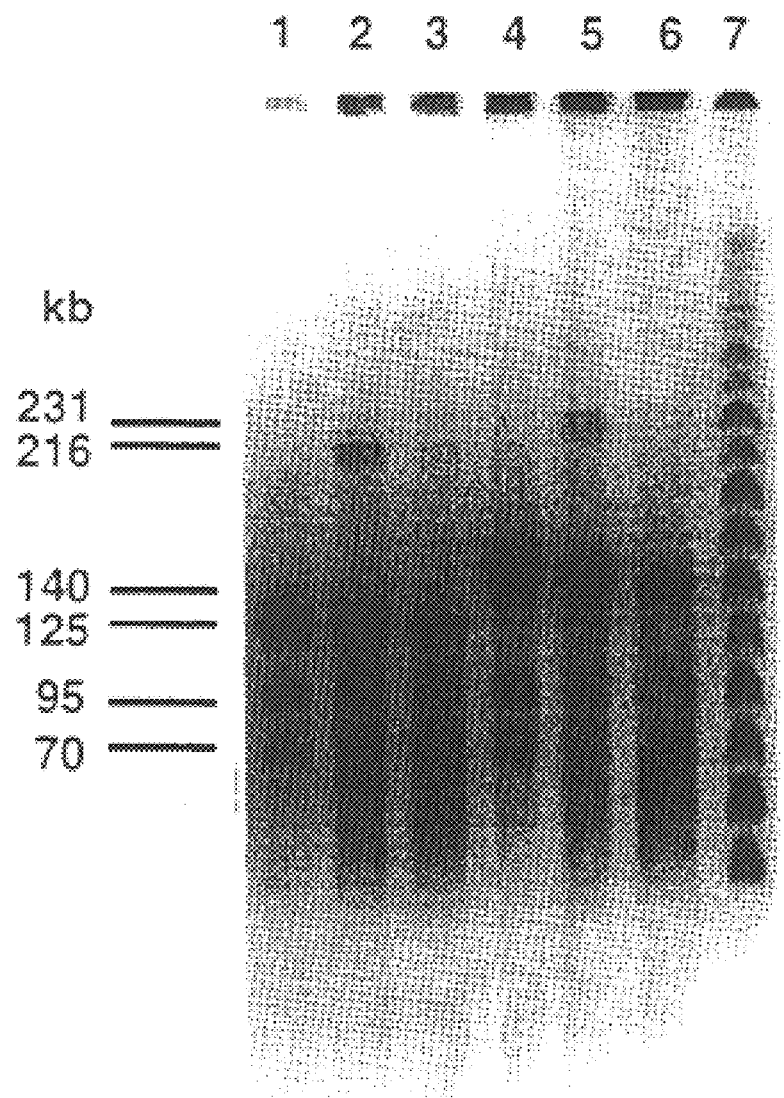
FIG. 2 Pulsed field gel electrophoresis stained with ethidium bromide. The BssHII-linearized alpha-satellite PACs of chromosome X (lanes 1–3, 125 kb) and chromosome 17 (lanes 4–6, 140 kb) were combined with a MluI fragment which contains the human HPRT gene locus (lanes 1–6, 95 kb). The long recombination product having the predictable lengths of 216 and 231 kb cannot be seen in the controls without Cre recombinase (lanes 1 and 4) and are clearly evident in the presence of the Cre recombinase (lanes 2 and 5, in, the presence of 1% LMP agarose). Reactions in which the reaction mixture was diluted more strongly with the aqueous solution (CreSS buffer) included an LMP agarose concentration of about 0.6% as well as a correspondingly reduced DNA concentration (lanes 3 and 6). The lower efficiency in the dilute recombination reactions refers to the fact that an appropriate agarose concentration and high DNA concentrations are decisive. Lane 7, 24 kb ladder consisting of half a disk of the MidRange PFG marker II, which has a thickness of 1 mm (New England Biolabs).
Figure 3:
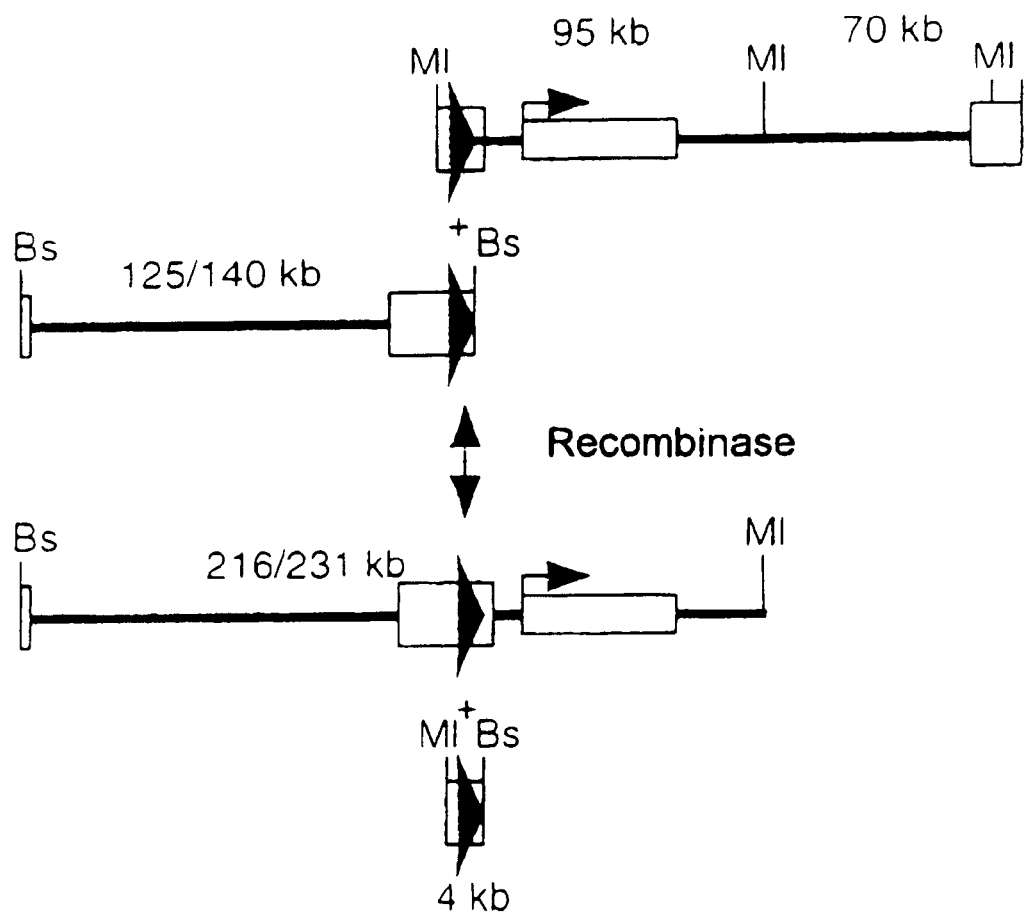
FIG. 3 Sequence-specific recombination in an agarose gel matrix: diagram of the recombination substrates (top) and products (bottom). The lox site (triangle) which is present in the PAC vector DNA (wide rectangle) recombines in an agarose gel matrix in the presence of Cre recombinase. Alpha-satellite DNA PACs of the human chromosomes X (125 kb) and 17 (140 kb), which were linearized with BssHII (Bs), are linked with a 95 kb MluL (MI) fragment originating from a 175 kb PAC which contains the intact human HPRT gene locus. The arrow indicates the direction of the primary transcript (narrow triangle) of 42 kb. Mlu fragments which contain no lox site are not shown as products. The small recombination product which resulted from 4 kb of overlapping PAC vector sequence has left the pulsed field gel (in FIG. 2).

(B) Combination of the PAC Clones by Means of Lox-Cre Recombinase in Melted Agarose The PACs to be joined are restriction-mapped and cleaved by select restriction nucleases to produce fragments which overlap in the lox site and point in opposite directions. Of many possible nucleases BssHII was used for the alpha-satellite PACs and MluI for the HPRT-gene PAC (FIG. 3). Complete cleavage is controlled with ¹⁄₁₀ of a little block (about 15 µl), which was cut out of the middle of the little block, by means of pulsed field gel electrophoresis and ethidium bromide staining. ⁹⁄₁₀ of the two little blocks with the DNA to be linked are incubated in CreSS buffer (50 mM Tris/HCl, pH 7.4, 10 mM $MgCl_2$, 30 mM NaCl, 0.75 mM spermidine/3HCl, 0.3 mM spermine/4HCl) for 4×30 minutes and then combined with 130 µl CreSS buffer in a 1.5 ml reaction vessel. As a result, a volume of about 400 µl and an LMP agarose concentration of about 1% form. The mixture is incubated at 67° C. with careful stirring using a pipette tip for 10 min. Thereafter, incubation is carried out at 42° C. for 5 min. Then, BSA (bovines serum albumin, 4 µl of a 10 mg/ml solution) and DTT (0.4 µl of a 1 M solution) are added with careful stirring. Incubation is continued at 42° C. for the next 30 minutes and careful stirring is carried out several times. In order to obtain a control of the material without recombination, 80 µl are carefully transferred to a little block mold using a pipette tip having a wide bore (about 3 mm). For the next 30 minutes, the incubation temperature is lowered step-wise to 37° C. with the repeated addition of 1 µl Cre recombinase (0.9 mg/ml) and subsequent careful but persistent stirring each, until a total of 6 µl Cre were added. The reaction mixture is heated again to 39° C. for two minutes and carefully placed in preheated little block molds (40° C.) which are disposed in an insulated chamber by using preheated pipette tips (45° C.) having a wide bore (3 mm). In this connection, attention has to be paid to the fact that the reaction mixture does not cool below 30° C., which would lead to the solidification of the agarose. The still melted reaction mixture is then incubated at 37° C. for 30 min. and at 32° C. for 30 min. By cooling down to room temperature, the little blocks solidify. The little blocks are treated with proteinase-K and can be stored in the proteinase-K buffer (contains SDS and EDTA, for long-term storage for a period of several months) or in TE. ¼ of a resulting little block is analyzed by means of pulsed field gel electrophoresis and ethidium bromide staining (FIG. 2).

Reference is made to the fact that another sequence-specific recombination, e.g. via the FLP recombinase with recognition sequence FRT, can also be carried out.

EXAMPLE 2

Production of Vectors According to the Invention (A) Production of the Monotelomeric Vector PT1

Figure 4:
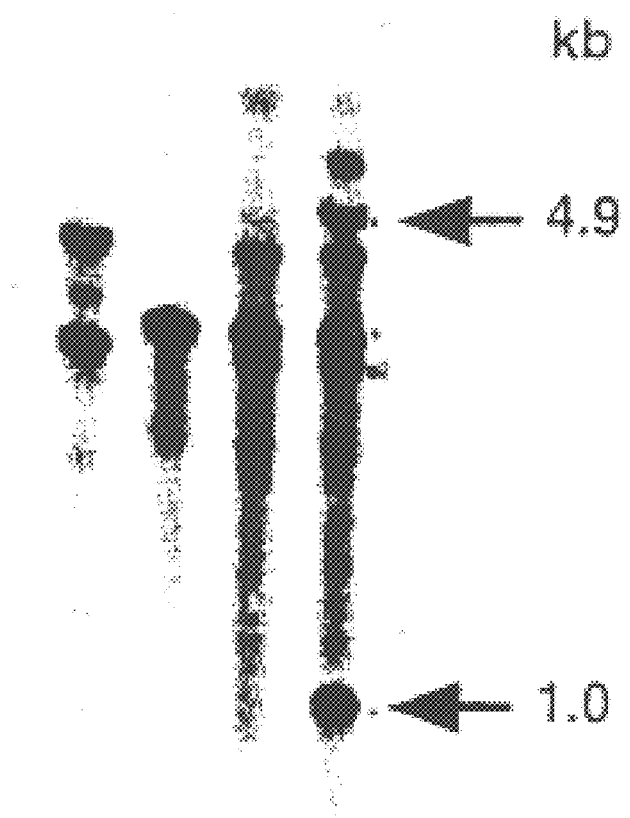
FIG. 4: Test for the suitability of the mutated lox site from PCYPAC2N for the use in an efficient in vitro recombination. Agarose gel electrophoresis and subsequent Southern blot. Hybridization was carried out with a 110 bp PCR fragment as a sample which was amplified with the primers LPF and LPR from PAC DNA. The PAC DNA was cleaved by the restriction nucleases EcoRI (lane 1) and HindIII (lane 2), phenolized and mixed equimolarly. The fragment mixtures were incubated according to standard methods (NENZYMES, DuPont company) in the absence (lane 3) and in the presence (lane 4) of Cre recombinase (0.9 mg/ml). It can clearly be seen that recombination products having the predictable length of 1 kb and 4.9 kb resulted. It follows from the estimated ratio of substrate bands to product bands that the in vitro efficiency of this mutated lox sequence of the PAC vector (sequence positions 2016–2049 of the gene library Acc. No. U09128) is comparable with the in vitro efficiency of the original loxP sequence.
Figure 5:
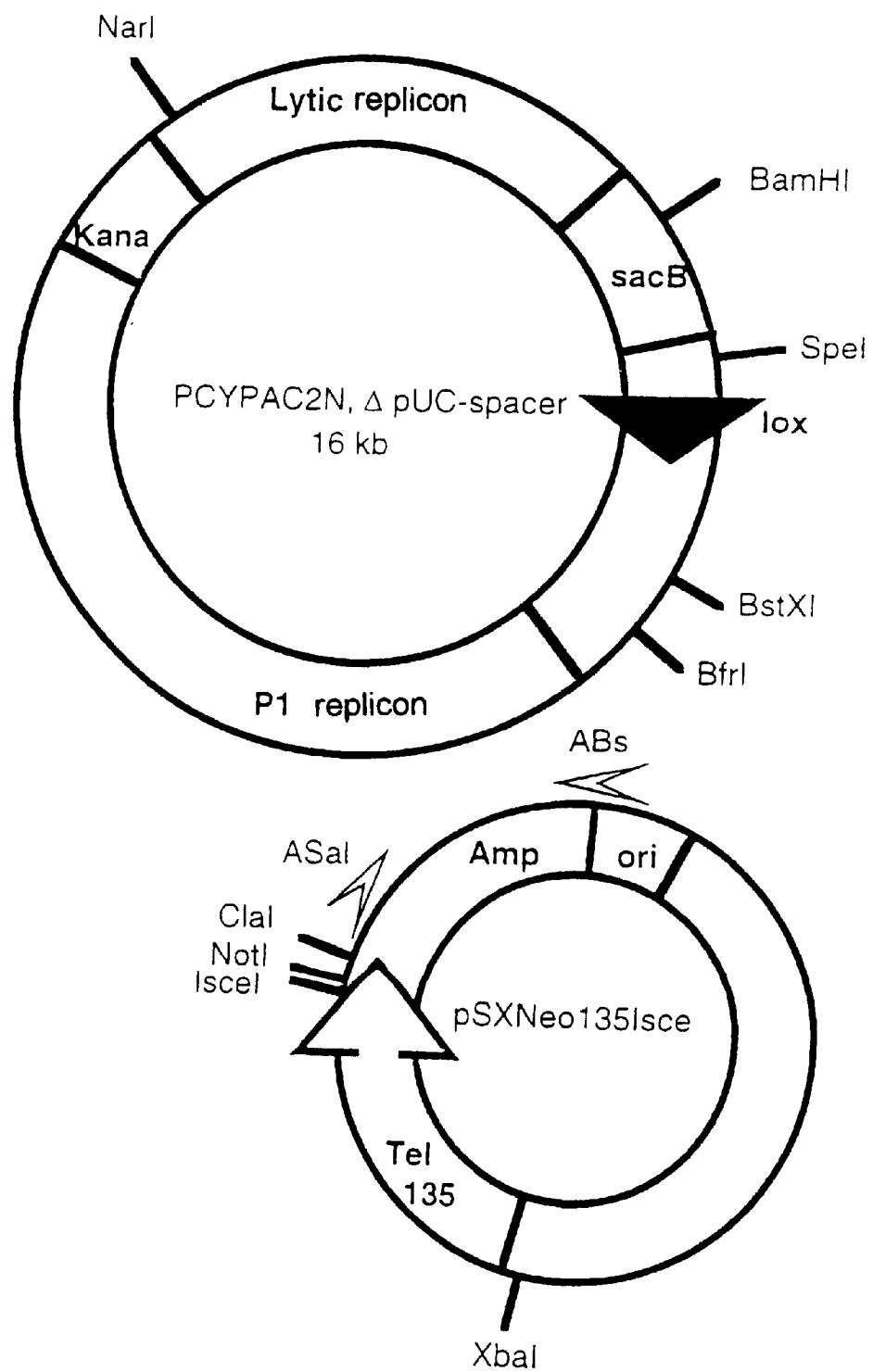
FIG. 5: Map of the employed starting plasmids for cloning the monotelomeric vectors PT1, PT1L, PT1LA, PT1LAS and the ditelomeric vector TPAT.

A 'unit copy' plasmid was prepared from the PAC vector PCYPAC2N (FIG. 5). Furthermore, the plurality of restriction nucleases cleavage sites was reduced. For this purpose, the lytic replicon of the PAC vector was removed together with the cloning site. In this way, the P1 phage replicon, the kanamycin resistance gene and the lox site are maintained on a fragment. The lox site originates from precursor clones of the vector PCYPAC2N and is still present as a cloning residue without function for PACs. In an in vivo reaction, two lox sites were joined for the production of the PAC vector. In order to check the suitability of the lox site present in PACs as a functional recombination site for an efficient recombination in melted agarose, in vitro recombination tests were carried out. This became particularly important, since the sequence of the lox site in the PAC vector differs from the originally disclosed lox sequence (sequence positions 2016–2049 of gene library Acc. No. U09128) and an efficient in vitro recombination of this sequence was not known (FIG. 4). For cloning the first telomere sequence, the PAC vector DNA was cleaved by restriction nucleases NarI and SpeI (Boehringer enzymes and buffers). Thereafter, the DNA was purified by ethanol precipitation, taken up in buffer for alkaline phosphatase and dephosphorylated for 30 min. (Boehringer). After a single phenolization, the 10.3 kb fragment was eluted after 12 h of running of the gel at 30 V in 0.5×TAE from a 1% agarose gel (LMP agarose, Gibco BRL) in the absence of U.V. radiation, purified using a Geneclean kit: and taken up in TE. About 10 ng DNA were ligated with the gel-eluted ClaI/XbaI telomere fragment of 0.9 kb, which was used in multiple excess, at 4 to 20° C. with T4-DNA ligase in a corresponding buffer in a volume of 30 μl overnight. 50% of the ligation batch were analyzed by means of agarose gel electrophoresis and ethidium bromide staining. The other 50% were dialyzed against distilled water (drop-dialyzing membrane, Gibco BRL) for 2 h and used for transforming 40 μl of electrocompetent cells (ElectroMAX DH10B Cells, Gibco BRL). The transformation was carried out in a 100 μl cuvette at 1.8 KV by electroporation. Kanamycin-resistant clones (30 μg/ml) were tested for the presence of the telomere fragment by means of PCR from bacterial colonies. For this purpose, the primers LPF and G438 were used (62° C., 30 cycles, Taq polymerase; cf. FIGS. 14 and 16). The expected 1.3 kb product could not be seen. Each of the 7 resistant clones had a mixture of PCR products having lengths of 600 to 800 bp instead. By subsequent restriction mapping from isolated plasmid DNA it could be shown that all of the clones have the full length of the original telomere fragment of 0.9 kb. The reduction in length during a PCR amplification which covers the telomere sequence had already been observed in the starting clone pSXneo135 (FIG. 5). It is due to the special, repetitive nature of the telomere sequence. If the (TTAGGG) units are strictly homologous with respect to one another, the PCR product will hardly be longer than 400 bp (plus surrounding sequences), irrespective of how long the actual telomere sequence is. This special PCR behavior of the strictly homologous telomere sequences can be used diagnostically to check the quality of the telomere sequence when the full length is simultaneously proved in a restriction mapping. In order to obtain sufficient amounts of DNA for the restriction analysis and subsequent cloning from the bacteria which carry 'unit copy' plasmids and thus have up to 50 times fewer plasmid molecules than e.g. conventional pUC vectors, 600 ml LB cultures were used for the alkaline lysis isolation. A rap of the vector PT1 is shown in FIG. 6.

(B) Production of the Monotelomeric Vector PT1L by Integration of a Synthetic Linker in PT1

For the subsequent integration of a second resistance gene (Amp) and the second telomere sequence as well as the availability of restriction sites cutting once for cloning genomic fragments (gene/centromer) or a selectable marker gene between the telomere sequences, a linker was integrated between lox site and P1 replicon (FIG. 7). In order to be able to use the same telomere fragment preparation which resulted in the cloning of PT1, a NarI site and an XbaI site were introduced. For the integration of the Amp gene and simultaneously for the presence of seldom cleaving restriction sites, a BssHII site and a SalI site were introduced. Two synthetic oligonucleotides PT21 and PT22 yield a double-stranded linker for this purpose (sequences in FIG. 16). The overhanging ends of the linker are ligated in given orientation into the singular BfrI and BstXI sites. For this purpose, 10 ng of the non-dephosphorylated PT1 DNA cleaved by BfrI/BstXI (Boehringer) were gel-eluted and used with 1 μg of non-phosphorylated linker DNA. (Transformation as described above). Two of the four clones analyzed by restriction mapping contained all of the new restriction sites. The only exception was initially the integrated NarI site (FIG. 8). The sequence used on the oligonucleotides corresponds to an NarI site which will only be cleaved if other NarI sites cleaved more effectively are made available in cis or trans. If ten times an excess of pBR328 is admixed to the cleavage reaction, the integrated NarI site can be cleaved satisfactorily (FIG. 11).

(C) Preparation of the Monotelomeric Vectors PT1LA and PT1LAS

In order to have two independent resistance genes between the telomere sequence ends and beginnings of a ditelomeric vector, the ampicillin resistance gene (Amp) was cloned from the vector SP73 (FIG. 5) into the newly created restriction sites BssHII and SalI of the PT1L vector. In this connection, special attention had to be paid to the fact that the 'multi copy' replication origin (ori) of the pBR plasmids, which is located in the vicinity of the 3' end of the ampicillin resistance gene, is not integrated into the 'unit copy' plasmid as well to keep the number of copies as small as possible. At the same time, the Amp fragment should border directly on ori to guarantee transcription termination signals of the Amp transcript. No suitable restriction sites which could be used for removal by cleavage and the subsequent cloning are located on the border between Amp and ori. It was possible to synthesize the oligonucleotides ASal and ABs, which were equipped with the restriction sites SalI (in 5' of Amp) and BssHII (in 3' of Amp) by changing individual nucleotides. The Amp gene was amplified on a 1260 bp fragment, the PCR product was subsequently cleaved at the ends by means of nucleases SalI and BssHII, gel-eluted, purified and cloned into the dephosphorylated, gel-eluted vector PT1L cleaved by SalI and BssHII. Two colonies were obtained which showed double resistance for ampicillin and kanamycin. Both colonies were positive for the PCR with primers G438 and LPF to control the presence of the first telomere sequence, positive for the PCR with primers ASal and ABs (corresponds to the resistance to ampicillin), and positive for the PCR with primers ABs and LPR (confirmation of the planned orientation). Of these, one clone (PT1LA, 12.1 kb) had the predicted structure in the restriction analysis and the other clone (PT1LAS, 13.9 kb) had integrated an additional 1.8 kb sequence at the 3' end of the Amp gene (FIGS. 9 and 10). In this connection, the primer binding site for ABs was directly maintained in the 3' of the Amp gene, but the BssHII site as such was displaced by the integrated sequence by 1.8 kb. The clone PT1LAS was obtained from the ligation reaction.

(D) Preparation of the Ditelomeric Vector PTAT from PT1LAS

For cloning the second telomere fragment, the restriction sites NarI and XbaI were introduced into the linker DNA of PT1L (and thus PT1LAS). The cleavage of the restriction site NarI became possible by admixture of ten times an excess of pBR328 plasmid (FIG. 11). The 13.9 kb fragment of the plasmid PT1LS, which was cleaved by NarI and XbaL, was dephosphorylated using alkaline phosphatase, phenolized once, eluted from 1% LMP agarose gel following electrophoresis, and purified by means of the Geneclean kit. The method was carried out as in the cloning of PT1. The ligation was checked (FIG. 12). Twelve doubly resistant clones (ampicillin and kanamycin) were subjected to restriction analysis by means of alkaline lysis after the isolation of plasmid DNA from 600 ml cultures. One of the resulting clones was analyzed and showed the expected 10.5 kb BamHI fragment which contains both telomere sequences and the P1 replicon. In order to check the entire structure of the ditelomeric vector PTAT, a comprehensive restriction analysis was carried out (FIG. 15). The predicted structure could be fully confirmed and the function of the extremely seldom cleaving IsceI sites at both telomere sequence ends was identified. This means that a plasmid is available which can be propagated stably to clone long fragments as chromosomal components and join them in melted agarose with a second stably cloned chromosomal component.

(E) Vector PTAT as a Basis for the Most Differing Applications

The 6.1 kb long NotI or IsceI fragment of PTAT which has telomere sequences at both ends, can be modified for various purposes. To this end, the integrated restriction sites XbaI, SalI and BssHII can be used as sites occurring once or as other sites. In addition, an MCS (multiple cloning site) can be introduced into one of the existing restriction sites. It should usefully contain recognition sequences of rather seldom cleaving restriction nucleases. Furthermore, existing restriction sites occurring several times could be modified by the introduction of mutations. It is also possible to introduce into the restriction sites further prokaryotic or eukaryotic selectable marker genes as well as genes, which can be used for the color/fluorescence identification of *E. coli* or mammalian cells or DNA fragments to detect MACs in living cells (e.g. via specific DNA recognition sequences of binding proteins which are linked to the gelly fish protein (GFP)). Another possibility of modification would be the cloning of a DNA fragment of PTAT or descendants, which contains both telomere sequences (e.g. the 6.1 kb NotI fragment), into another existing vector (e.g. BAC vectors, other PAC vectors or other vectors) or into existing genomic clones. This possibility is particularly facilitated in that selection can be made for the presence of the fragment after recloning (ampicillin resistance). Improved PTAT versions could then be used for the cloning or recloning of a long genomic segment (e.g. genomic copy of a gene or centromer candidate sequence).

If a genomic copy of the human HPRT gene of Example 1 is initially cloned into PTAT or its descendants on a long fragment (or other selectable mammalian genes), the resulting chromosome arm which contains telomeres at both ends can be linked in melted agarose with any circular centromer candidate sequences which contain a suitable recombination site (in the case of PTAT this would be e.g. every PAC clone of a genomic library which has been prepared with the PCYPAC2N vector). The structure of the MAC constructs would already be known from the analysis of the individual components (FIG. 18). Because of the recombination in melted agarose the recombination products are obtained in the form of little agarose blocks, so that another advantage for obtaining the recombination product results. If both components are inserted as circular DNA in the recombination reaction, large circular products will form. They can be fully freed from the small part of partially degraded DNA, which can hardly be avoided, by subsequent pulsed field gel electrophoresis. Only intact DNA is retained in the little block. Following cleavage directly at the telomere sequence ends, only two well separable fragments run into the gel, the 'small' ditelomeric fragment which did not recombine and the recombined 'long' ditelomeric MAC construct. The amount of circular component which did not recombine remains in the little block. The MAC which contains the most efficient centromer can be determined by transfection of various constructs. A 'best' centromer identified in this way would be cloned into improved PTAT versions to obtain a basic MAC vector TZT (telomere—centromer—telomere). It can be combined in melted agarose with any circular DNA component which contains a suitable recombination site (depending on the design of TZT this would be a lox site or descendants in combination with the: recombinase Cre, an FRT site in combination with the recombinase Flp, or both at the same time, or other sequence-specific recombination sites for an efficient in vitro application) (FIG. 19).

Table 1

Synthetic Oligonucleotides

G438: 5'-GGCCGCGCTAGGGATAACAGGGTAATATA-3'(SEQ ID NO: 1)

G439: 5'-GGCCTATATTACCCTGTTATCCCTAGCGC-3' (SEQ ID NO: 2)

By annealing of G438 with G439 a double-stranded DNA fragment forms which contains an IsceI consensus sequence and can be cloned into a NotI site.

LPF: 5'-GAAACGGCCTTAACGACGTAGTCG-3'(SEQ ID NO: 3)

LPR: 5'-ATGATAAGCTGTCAAACATGAGAATTG-3' (SEQ ID NO: 4)

PCR primers for amplifying around 110 bp of the PAC vector which contain the lox site (nucleotide positions 1973–2082 gene library Acc. No. U09128).

ASal: 5'-GCGAGTCGACAGGGCCTCGTGATACG-3' (SEQ ID NO: 5)

ABs: 5'-GATTGCGCGCAGAAAAAAAGGATCTC-3' (SEQ ID NO: 6)

PCR primers for amplifying around 1263 bp of the pSP73 vector (nucleotide positions 939–2202 gene library Acc. No. X65333) with the ampicillin resistance gene. The sequences of the primers are modified in individual bases to introduce a BssHII cleavage site (ABs) and a SalI cleavage site (ASal) at the ends of the PCR product.

Kf: 5'-GGAAAACAGCATTCCAGGTATTAG-3'(SEQ ID NO: 7)
Kr: 5'-CCATGAGTGACGACTGAATCCG-3'(SEQ ID NO: 8)

PCR primers for amplifying around 282 bp of the kanamycin resistance gene of the PAC vector (nucleotide positions 10683–10965 of the gene library Acc. No. U09128).

PT21:
5'-TTAAGGCGCCAAATCTAGAGGATCCGCGCGCAAGAGGTCGACCTAA-3'(SEQ ID NO: 9)

PT22:
5'-GTCGACCTCTTGCGCGCGGATCCTCTAGATTTGGCGCC-3'(SEQ ID NO : 10)

PT21 and PT22 anneal to give a double-stranded DNA fragment which was used as a linker to introduce the restriction sites NarI, XbaI, BamHI, BssHII and SalI between the restriction sites BfrI (nucleotide position 3309 in the precursor Acc. No. U09128) and BstXI (nucleotide position 2917 in the precursor Acc. No. U09128) of the vector PT1.

What is claimed is:

1. A method for producing a DNA construct, the method comprising:
   (a) providing a recombinase;
   (b) providing DNAs for recombination, each DNA comprising a sequence specific for the recombinase;
   (c) providing an agarose at a temperature which maintains the agarose in a sufficiently liquid state to permit sufficiently homogeneous mixing of the DNAs and the recombinase to permit recombination of the DNAs to form the DNA construct;
   (d) combining the recombinase and the DNAs in the agarose for a time and under conditions sufficient to effect recombination of the DNAs to form the DNA construct;
   (e) separating the DNA construct from the other DNA in the agarose.

2. The method of claim 1 wherein the agarose melts at a temperature of about 30° C.

3. The method of claim 1 wherein the agarose is maintained in a liquid state.

4. The method of claim 1 wherein the DNA construct has a length of 200 kb or greater.

5. The method of claim 1 wherein:
   (a) the DNAs comprise lox sequences; and
   (b) the recombinase comprises a Cre recombinase.

6. The method of claim 1 wherein:
   (a) the DNAs comprise FRT sequences; and
   (b) the recombinase comprises an FLP recombinase.

7. The method of claim 1 wherein two DNAs are provided in step (b), one DNA being linear and the other being circular.

8. The method of claim 1 wherein two linear DNAs are provided in step (b).

9. The method of claim 1 wherein two circular DNAs are provided in step (b).

10. The method of claim 1 wherein the wherein step (e) comprises substeps:
    (i) cleaving DNA other than the DNA construct to yield DNA fragments;
    (ii) solidifying the gel to form a solidified gel comprising the DNA construct and the DNA fragments; and
    (iii) in the solidified gel, separating the DNA fragments from the DNA construct by gel electrophoresis.

11. The method of claim 10 wherein substep (i) is accomplished by adding to the agarose restriction enzymes specific for restriction sites not present on the DNA construct.

12. The method of claim 10 further comprising the step of obtaining the DNA construct from the gel following substep (iii).

13. A solidified agarose gel comprising the DNA construct, wherein the gel is prepared by a process comprising:
    (a) performing the steps of the method of claim 10; and
    (b) physically separating gel comprising the DNA construct from gel comprising DNA fragments.

14. A method for producing a DNA construct, the method comprising:
    (a) providing a recombinase;
    (b) providing DNAs for recombination, each DNA comprising a sequence specific for the recombinase;
    (c) providing an agarose at a temperature which maintains the agarose in a sufficiently liquid state to permit sufficiently homogeneous mixing of the DNAs and the recombinase to permit recombination of the DNAs to form the DNA construct;
    (d) combining the recombinase and the DNAs in the agarose for a time and under conditions sufficient to effect recombination of the DNAs to form the DNA construct;
    (e) obtaining the DNA construct by:
       (i) adding to the gel restriction enzymes which cleave DNA other than the DNA construct to yield DNA fragments;
       (ii) solidifying the gel to from a solidified gel comprising the DNA construct and the DNA fragments;
       (iii) in the solidified gel, separating the DNA fragments from the DNA construct by gel electrophoresis; and
       (iv) obtaining the DNA construct from the gel.

15. The method of claim 14 wherein the agarose melts at a temperature of about 30° C.

* * * * *

UNITED STATES PATENT AND TRADEMARK OFFICE
CERTIFICATE OF CORRECTION

PATENT NO. : 6,331,397 B1
DATED : December 18, 2001
INVENTOR(S) : Schindelhauer et al.

It is certified that error appears in the above-identified patent and that said Letters Patent is hereby corrected as shown below:

Drawings,
Figure 14, "ASa " should be -- ASaI --

Column 1,
Line 8, change "purposes" to -- purpose --
Line 20, change "These" to -- There --
Line 33, start new paragraph with "Thus, ...."

Column 3,
Line 1, start new paragraph with "The ...."
Line 49, "in, the" should be -- in the --

Column 4,
Line 46, "3109" should be -- 3309 --

Column 5,
Line 29, change "1-9," to -- 1-9; --
Line 30, change "12-20-," to -- 12-20; --
Line 31, change "XbaI," to -- XbaI; --
Line 32, change "BamII," to -- BamII; --
Line 52, "1776" should be -- 1716 --
Line 59, change "lanes, 2 7" to -- lanes 2,7 --
Line 61, change "XbaI," to -- XbaI; --

Column 7,
Line 8, change "enzymes:" to -- enzymes; --
Line 63, "Lox" should be -- lox --

Column 8,
Line 1, "a95" should be -- a 95 --
Line 35, "Lox" should be -- lox --

UNITED STATES PATENT AND TRADEMARK OFFICE
CERTIFICATE OF CORRECTION

PATENT NO.     : 6,331,397 B1
DATED          : December 18, 2001
INVENTOR(S)    : Schindelhauer et al.

It is certified that error appears in the above-identified patent and that said Letters Patent is hereby corrected as shown below:

<u>Column 10,</u>
Line 14, "rap" should be -- map --

<u>Column 12,</u>
Line 35, "the: recom-" should be -- the recom- --

<u>Column 18,</u>
Line 35, change "from" to -- form --.

Signed and Sealed this

Eleventh Day of June, 2002

*Attest:*

*Attesting Officer*

JAMES E. ROGAN
*Director of the United States Patent and Trademark Office*